(12) United States Patent
Justin et al.

(10) Patent No.: US 6,406,479 B1
(45) Date of Patent: Jun. 18, 2002

(54) METHOD FOR REPAIRING A MENISCAL TEAR IN A KNEE

(76) Inventors: Daniel F. Justin, 1015 N. 520 West, No. 3, Logan, UT (US) 84341; Thomas F. Winters, 2031 Venetian Way, Winter Park, FL (US) 32789

( * ) Notice: Subject to any disclaimer, the term of this patent is extended or adjusted under 35 U.S.C. 154(b) by 0 days.

(21) Appl. No.: 09/314,431

(22) Filed: May 18, 1999

Related U.S. Application Data

(62) Division of application No. 08/867,071, filed on Jun. 2, 1997, now Pat. No. 5,980,524.

(51) Int. Cl.[7] ............................................. A61B 17/58
(52) U.S. Cl. .......................... 606/104; 606/72; 606/75; 606/76; 606/213
(58) Field of Search .................... 606/75, 104, 216, 606/217, 218, 153, 154, 76, 77, 72, 213

(56) References Cited

U.S. PATENT DOCUMENTS

| | | |
|---|---|---|
| 146,023 A | 12/1873 | Russell |
| 4,175,555 A | 11/1979 | Herbert |
| 4,873,976 A | 10/1989 | Schreiber |
| 4,884,572 A | 12/1989 | Bays et al. |
| 4,895,148 A | 1/1990 | Bays et al. |
| 5,059,206 A | 10/1991 | Winters |
| 5,085,550 A | 2/1992 | Lin |
| 5,152,790 A | 10/1992 | Rosenberg et al. |
| 5,169,400 A | 12/1992 | Mühling et al. |
| 5,246,441 A | 9/1993 | Ross et al. |
| 5,259,398 A | 11/1993 | Vrespa |
| RE34,871 E | 3/1995 | McGuire et al. |
| 5,403,136 A | 4/1995 | Mathys |
| 5,492,442 A | 2/1996 | Lasner |
| 5,632,745 A | 5/1997 | Schwartz |
| 5,723,008 A * | 3/1998 | Gordon ........................ 606/75 |
| 5,749,874 A | 5/1998 | Schwartz |

FOREIGN PATENT DOCUMENTS

WO    PCT 94/16636    8/1994

OTHER PUBLICATIONS

Kevin R. Stone, M.D., WIlliam G. Rodkey, D.V.M., Richard J. Webber, PH.D., Luann McKinney, D.V.M. and J. Richard Steaman, M.D., *Future Directions—Collagen–Based Prostheses for Meniscal Regneration,* Clinincal Orthopaedics and Related Research, No. 252, Mar. 1990, pp. 129–135.

* cited by examiner

Primary Examiner—Michael Buiz
Assistant Examiner—Julian W. Woo
(74) Attorney, Agent, or Firm—Allen, Dyer, Doppelt, Milbrath & Gilchrist, P.A.

(57) ABSTRACT

A fastener for use in soft tissue repair includes a resorbable polymer or suture core having one or more collagen bands in surrounding relation to the core. The bands are expandable between a dehydrated state for insertion and a hydrated state for healing, and are dimensioned and positioned to bring two sides of a tear into apposition to promote healing of the tear. The fastener insertion method includes driving an elongated tube across the tear, inserting a fastener down the tube until it breaches the tear, and removing the tube, leaving the fastener in position to expand and promote healing of the tear.

10 Claims, 8 Drawing Sheets

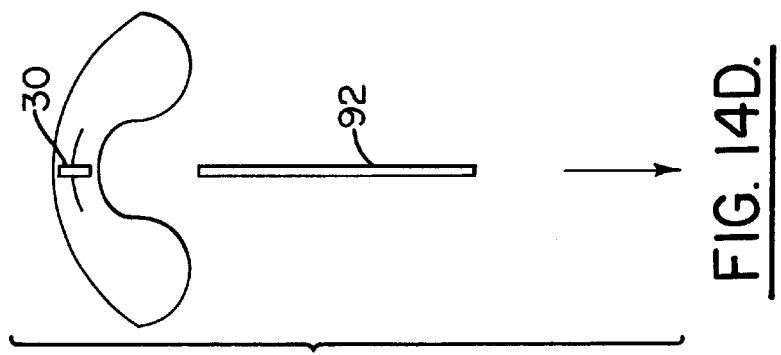
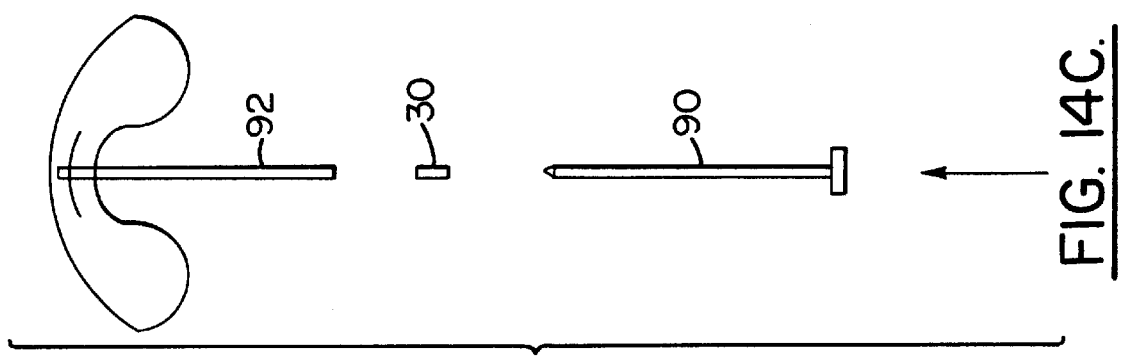
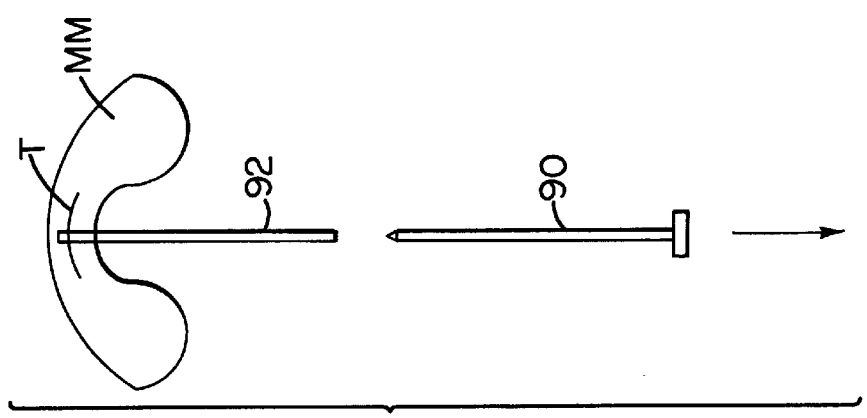
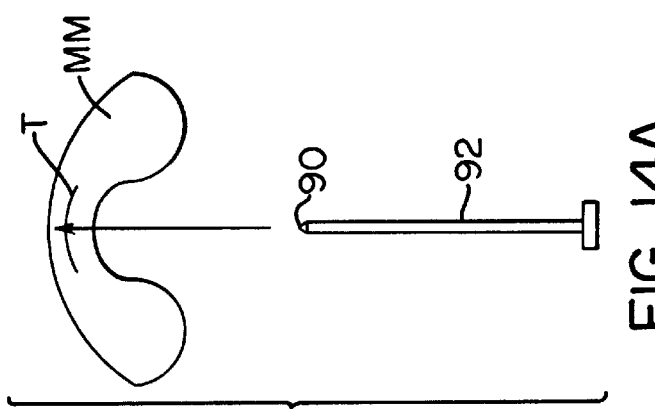

METHOD FOR REPAIRING A MENISCAL TEAR IN A KNEE

CROSS REFERENCE TO RELATED APPLICATION

This application is a divisional of application Ser. No. 08/867,071 filed Jun. 2, 1997, now U.S. Pat. No. 5,980,524, commonly owned with the present application.

BACKGROUND OF THE INVENTION

1. Field of the Invention

The present invention relates to surgical devices and methods for repairing tissue tears and, more particularly, to a device and method for repairing a meniscal tear in a knee.

2. Description of Related Art

The menisci of the knee are C-shaped disks of cartilaginous tissue interposed between the condyles of the tibia and the femur. They are actually extensions of the tibia that serve to deepen the articular surfaces of the tibial plateau to accommodate better the condyles of the femur (see FIG. 1). The material of the menisci is collagenous, and the fibers are oriented generally circumferentially.

As the menisci were long considered functionless remains of leg muscle, injury to this tissue had been treated by their total removal, called meniscectomy. A better understanding of these structures, combined with improvements in arthroscopic surgical techniques, has led to the development of meniscal repair techniques.

Posterior peripheral tears of the menisci may be treated by an open technique, wherein sutures are placed along the tear. An arthroscopic technique may also comprise placing sutures along the tear, but in this method through a cannula.

There are a number of fastener-type devices that are known in the art. A surgical fastener is disclosed by Screiber (U.S. Pat. No. 4,873,976) that comprises a shaft having at least one barb for locking the shaft in place when inserted into soft tissue. Also described is an applicator consisting of a cylinder into which the fastener is placed and out of which the fastener is pushed when positioned at the tear site.

Bays et al. (U.S. Pat. Nos. 4,884,572 and 4,895,148) describe a surgical-repair tack and applicator and method of using them. The tack has a barb member and is made of biodegradable material having a degradation time selected to coincide with the healing time of the tissue. In an alternate embodiment, the tack's barb comprises a continuous helical barb.

The method and apparatus for repairing a meniscal tear disclosed by Winters (U.S. Pat. No. 5,059,206) comprises a fastener having protrusions or barbs that is applied to a meniscal tear with a delivery device. The delivery device has a flexible tip that is manipulable through a curved radius to enable the surgeon to insert the device into the central part of the knee and then extend the fastener radially outward into and across a meniscal tear.

A fastener, driving device, and method have been described by Justin and Winters (U.S. Pat. Nos. 5,569,252 and 5,xxx,xxx) wherein the fastener has a helical protrusion that is advanced across a tear in a screwing motion. In the latter patent, the protrusion has a variable-pitch for bringing two sides of the tear into apposition as the fastener is advanced across the tear. The fastener material preferably is a bioabsorbable, biocompatible, nontoxic plastic that is specifically designed to bioabsorb generally within the time span of the healing process. A delivery device for introducing the fastener was also provided that includes an elongated needle rotationally coupled with the fastener.

Stone et al. (*Clin. Orthopaed. Rel. Res.*, No. 252, March 1990) introduced a resorbable collagen template for induced meniscal regeneration.

No method of repairing meniscal tissue with a device made from a core of bioabsorbable material and outer tubes or bands of expanding collagen is known to have been disclosed, however.

SUMMARY OF THE INVENTION

It is an object of the present invention to provide a bioabsorbable fastener and method for repairing a tear in soft tissue.

It is a further object to provide such a fastener that is made from a nontoxic, biocompatible, bioabsorbable material.

It is an additional object to provide such a fastener having a shape designed to compress the tear.

It is another object to provide such a fastener shaped to resist forces tending to pull apart the tear during the healing process.

It is yet a further object to provide such a fastener that expands following introduction across the tear.

These and other objects are attained with the fastener and method of the present invention. The fastener of the present invention is designed for repairing a tear in soft tissue of a patient, a particular exemplary embodiment comprising a meniscal tear in a knee.

The fastener in a first embodiment comprises an elongated core that has a distal portion that has a narrowing cross section toward a pointed distal end. Such a shape is for facilitating an insertion of the fastener into soft tissue. The core also has a narrowed central portion that extends between the proximal end and the distal portion.

The fastener additionally comprises a collagen band that is positioned in surrounding relation to the core's central portion. The collagen band is expandable between a dehydrated state for insertion and a hydrated state for healing. This collagen band is preferably shaped to bring two opposing sides of the tear into apposition, which promotes healing. The swelling caused by hydration creates an interference fit between the fastener and the soft tissue, which retains the fastener in position and resists a force tending to remove it therefrom.

In a preferred embodiment, the core material comprises a material that is biocompatible with the soft tissue of the patient and has a rigidity sufficient to support movement. The polymer core material is specifically designed to be biodegradable within a first time span greater than or equal to a second time span over which the sides of the tear can knit together. This feature permits the fastener to remain in place for as long as required for the tear to heal, but ultimately to be bioabsorbed and be dissipated harmlessly into the patient's system.

Alternatively, the core material comprises suture material that is bioresorbable.

In another embodiment the fastener comprises a unitary material, such as only rigid polymer or only collagen, and has means at the distal and proximal ends for holding the two sides of the tear in apposition. Such means may comprise barb-shaped protrusions or split sections that are biased to flare open when not under tension.

The method of the present invention is for repairing a tear in soft tissue of a patient. The method comprises the steps of driving a trocar across the tear in a direction generally normal to the tear and passing a tube over the trocar to a position wherein the tube breaches the tear. Next the trocar is removed from the soft tissue. A fastener containing collagen, or some other expandable polymer, such as described above in a dehydrated state is then introduced into the tube and pushed to a position adjacent a distal end of the tube. Next the tube is removed from the soft tissue, leaving the fastener in position to breach the tear.

The fastener is permitted to hydrate in situ, which causes the collagen band to swell, bringing the opposing sides of the tear into apposition and forming an interference fit between the fastener and the soft tissue. As described above, this serves to retain the fastener in position.

In one of the embodiments of the fastener described above, which comprises a rigid polymer without collagen, after positioning, the shape of the fastener holds the two sides of the tear together.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIGS. 14 schematically illustrates the method of introducing the fasteners of the present invention. FIG. 14A shows the cannula and trocar insertion; FIG. 14B the trocar removal; FIG. 14C the implant insertion; and FIG. 14D the cannula removal.

DETAILED DESCRIPTION OF THE PREFERRED EMBODIMENTS

A description of the preferred embodiments of the present invention will now be presented with reference to FIGS. 1–20.

Figure 1:
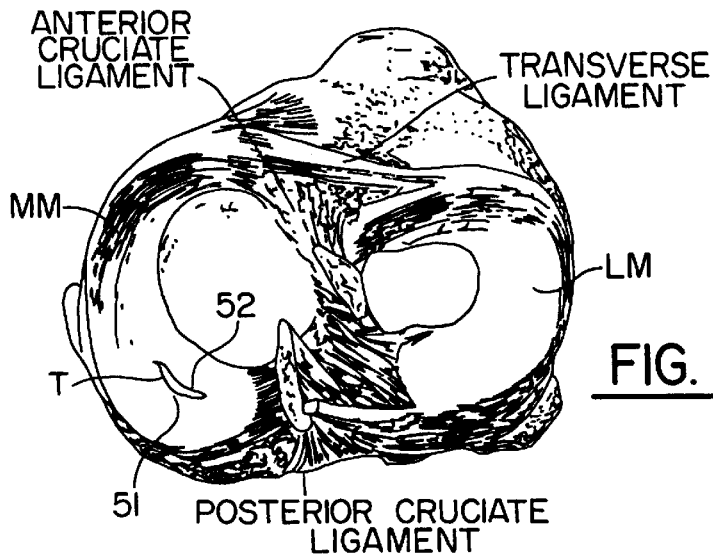
FIG. 1 illustrates the anatomy of a human knee in cross section, showing a tear in the medial meniscus.

The preferred exemplary embodiments of the present invention comprise a fastener and method for repairing a knee meniscal tear in a human patient. FIG. 1 illustrates a cross section of a human knee, showing the medial MM and lateral LM menisci and a tear T in the medial meniscus MM, the tear T having two sides S1 and S2.

The Fastener

Figure 2:
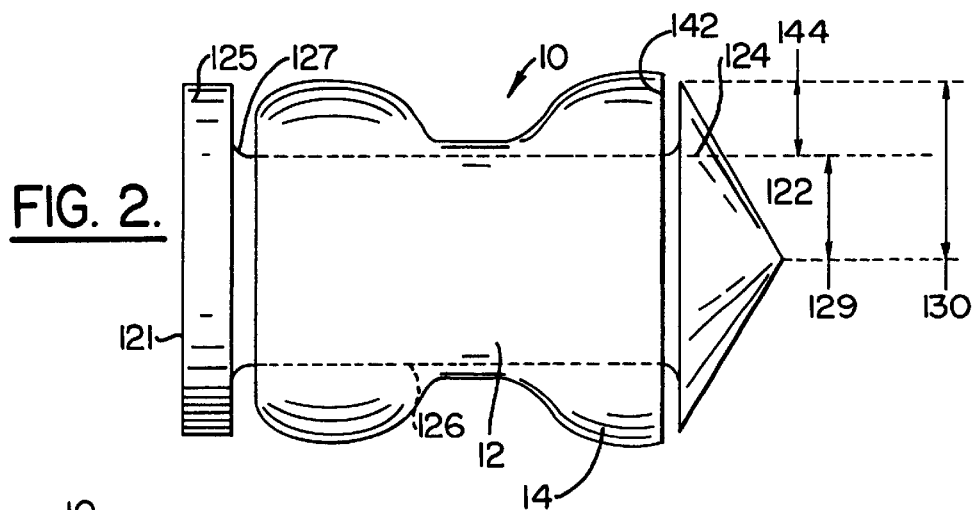
FIG. 2 is a perspective side view of a first embodiment of the fastener having a rigid polymer core and one collagen band in a dehydrated state.
Figure 3:
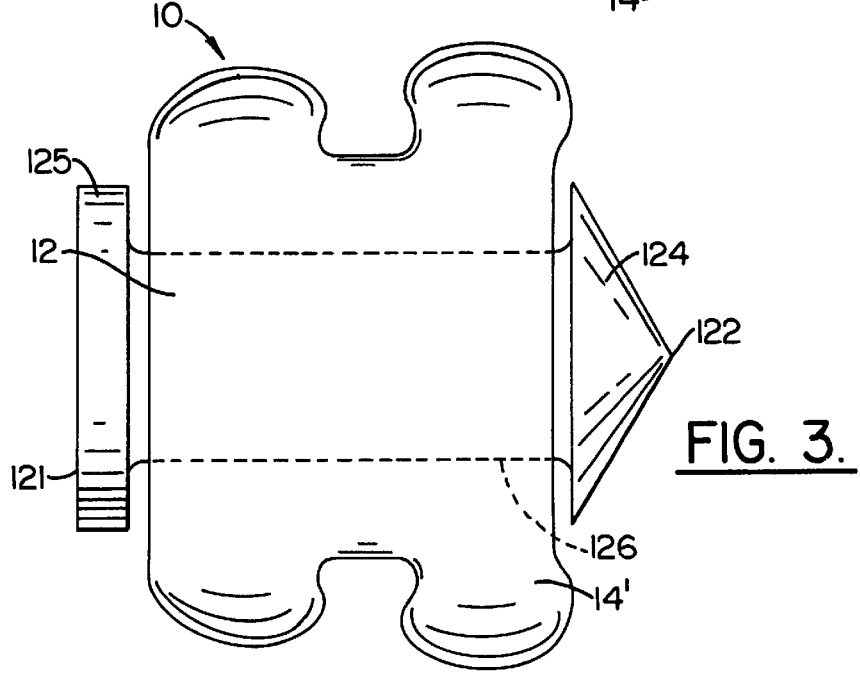
FIG. 3 is a perspective side view of the embodiment of FIG. 2 in a hydrated state.
Figure 4:
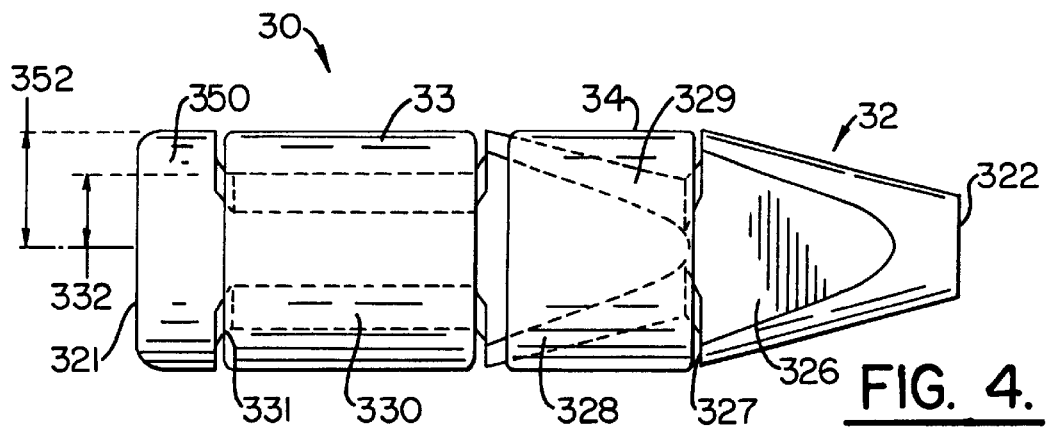
FIG. 4 is a perspective side view of a second embodiment of the fastener having a rigid polymer core and two collagen bands in a dehydrated state.
Figure 5:
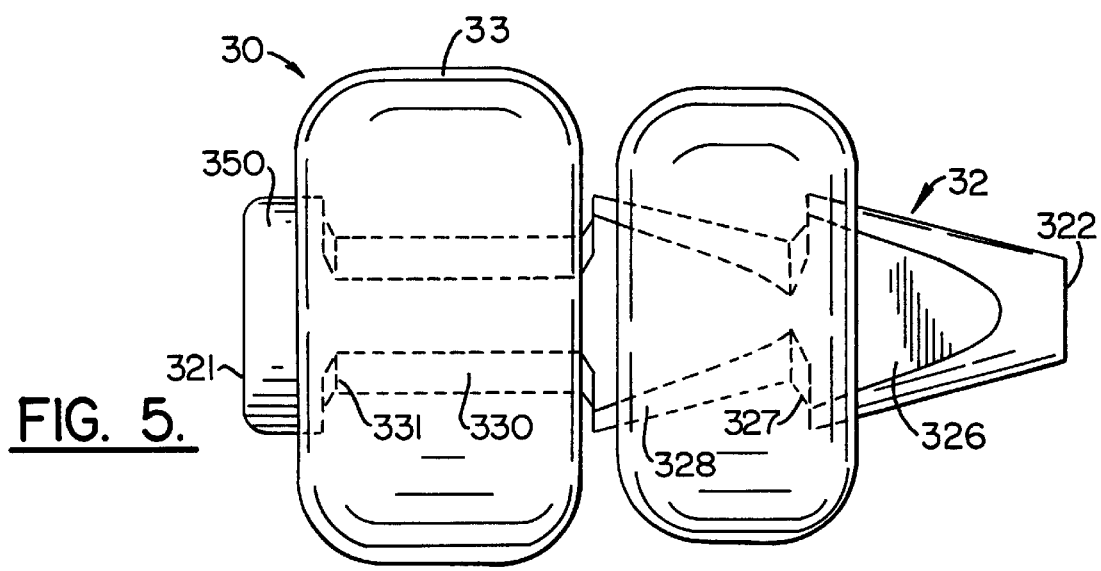
FIG. 5 is a perspective side view of the embodiment of FIG. 4 in a hydrated state.

A first embodiment of the fastener of the present invention is shown in FIGS. 2 and 3. The fastener 10 comprises an elongated core 12 that has a distal portion 124 that has a narrowing cross section toward a pointed distal end 122. This pointed distal end 122 facilitates the insertion of the fastener 10 into soft tissue. Preferably the distal portion 124 is conical in shape.

A narrowed central portion 126 extends between the proximal end 121 and the distal portion 124.

The core 12 further has a proximal portion 125 that extends from the proximal end 121 to a proximal end 127 of the core central portion 126. The proximal portion 125 has a radius that is larger than the central portion's radius.

A band 14 of polymer that expands upon hydration is positioned in surrounding relation to the core's central portion 126. Preferably the collagen band 14 has a thickness 144 at a distal end 142 that is approximately equal to the difference between the radius 129 of the core's central portion 126 and the radius 130 of the proximal end 123 of the core's distal portion 126. These dimensions form a generally smooth outer surface, which facilitates insertion.

The collagen band 14 is expandable between a dehydrated state for insertion (FIG. 2) and a hydrated state (FIG. 3) for healing. The band 14 is also shaped to bring two opposing sides S1,S2 of the tear T into apposition, which promotes healing and forms an interference fit between the fastener 10 and the soft tissue MM for retaining the fastener 10 in position.

An exemplary embodiment of the shape of the collagen band 14 comprises a generally hourglass-shaped band, which under hydration swells to a bibbed band 14' for compressing the tear T.

A preferred band polymer in this and the other of the following alternate embodiments comprises collagen; in a most preferred embodiment the collagen comprises a cross-linked bovine collagen.

The core material in this embodiment comprises a collagen or a bioabsorbable plastic biocompatible with the soft tissue of the patient. (A similar material will be intended when a noncollagen polymer is referred to.) Exemplary materials include a nontoxic blend of polycaprolactone and polyglycolide, a blend of polylactide and polyglycolide, pure polydioxanone, poly(ethylene oxide): poly-(butylene terephthalate), polyorthoester, polyhydroxybutyrate, or cross-linked collagen. The material is designed to be sufficiently flexible and strong to withstand natural knee movement during healing. The material is also designed to be biodegradable within a first time span greater than or equal to a second time span over which the sides S1,S2 of the tear T can knit together. In other words, the material is resorbed over a time span commensurate with the healing process, so that, once the tear T is healed, the fastener can gradually degrade, leaving a healed meniscus with no foreign material embedded therein.

In a second embodiment, the fastener 30 comprises an elongated core 32 that has a first conical portion 326 that has a narrowing cross section toward the distal end 322. As previously, the fastener's insertion into soft tissue is facilitated by this narrowed distal end 322.

The core 32 also has a second generally conical portion 328 that has a narrowing cross section toward the proximal end 327 of the first conical portion 326. A narrowed central portion 330 extends between the proximal end 321 and the second conical portion 328. The core 32 further has a proximal portion 350 that extends from the proximal end 321 to a proximal end 331 of the core's central portion 330. This proximal portion 350 has a radius 352 that is larger than the central portion's radius 332.

A first collagen band 33 is positioned in surrounding relation to the core's central portion 330, and a second collagen band 34 is positioned in surrounding relation to at least a distal section 329 of the second conical portion 328. Preferably the collagen bands 33,34 have a thickness adapted for forming a generally smooth outer surface of the fastener 30, which facilitates insertion.

As with the first embodiment, the collagen bands 33,34 are expandable between a dehydrated state (FIG. 4) for insertion and a hydrated state (FIG. 5) for healing. In this embodiment the collagen bands 33,34 when hydrated form a bilobed structure that serve to bring the two opposing sides S1,S2 of the tear T into apposition for promoting healing and also form an interference fit with the soft tissue MM, which assists in retaining the fastener 30 in position.

Figure 6:
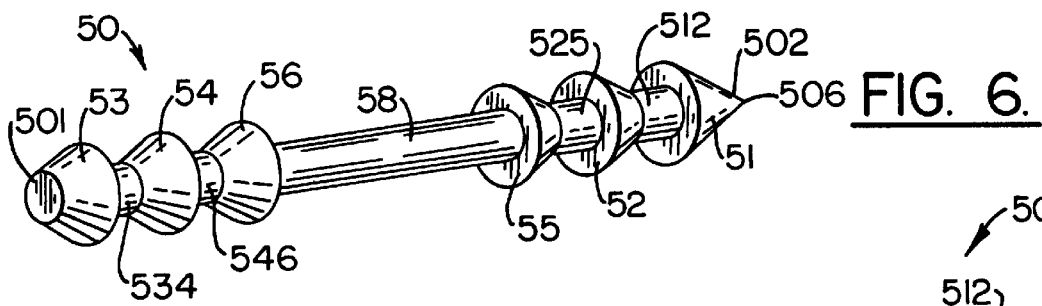
FIG. 6 is a perspective side view of a third embodiment, an all-collagen fastener with barbs, in a dehydrated state.
Figure 7:
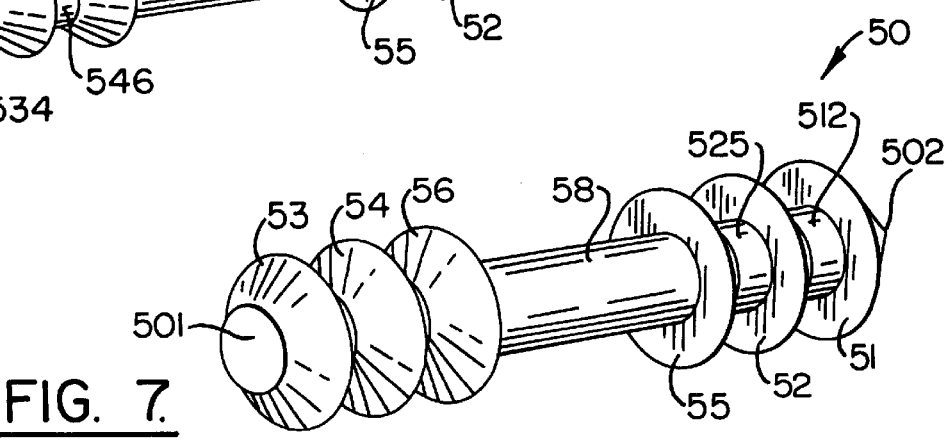
FIG. 7 is a perspective side view of the embodiment of FIG. 6 in a hydrated state.

A third embodiment of the fastener 50, which is illustrated in FIGS. 6 and 7, has a first generally conical portion 51 that narrows toward the distal end 502, which has a pointed tip 506. Fastener 50 also has a second generally conical portion 52 that is proximal of and narrows toward the first conical portion 51. In a preferred embodiment, the fastener 50 further has a fifth generally conical portion 55 that is proximal of and narrows toward the second conical portion 52.

Fastener 50 has at its proximal end 501 a third generally conical portion 53 that narrows toward the proximal end 501, a fourth generally conical portion 54 that is distal of and narrows toward the third conical portion 53, and a sixth generally conical portion 56 is distal of and narrows toward the fourth conical portion 54.

A narrowed, generally cylindrical central portion 58 extends between the fifth 55 and the sixth 56 conical portions. In a preferred embodiment, narrowed, generally cylindrical central portions 512, 525, 534, 546 extend between, respectively, conical portions 51–52, 52–55, 53–54, 54–56.

Preferably the fastener 50 comprises a polymer that expands upon hydration, such as the collagen material discussed previously. The fastener material is expandable between a dehydrated state (FIG. 6) for insertion and a hydrated state (FIG. 7) for healing. In use the expanded hydrated conical portions bring the two opposing sides S1,S2 of the tear T into apposition and form an interference fit within the soft tissue MM to resist a removal of the fastener 50 therefrom, as the conical portions form barblike protrusions that tend to anchor the fastener 50 within the tissue T.

Figure 8:
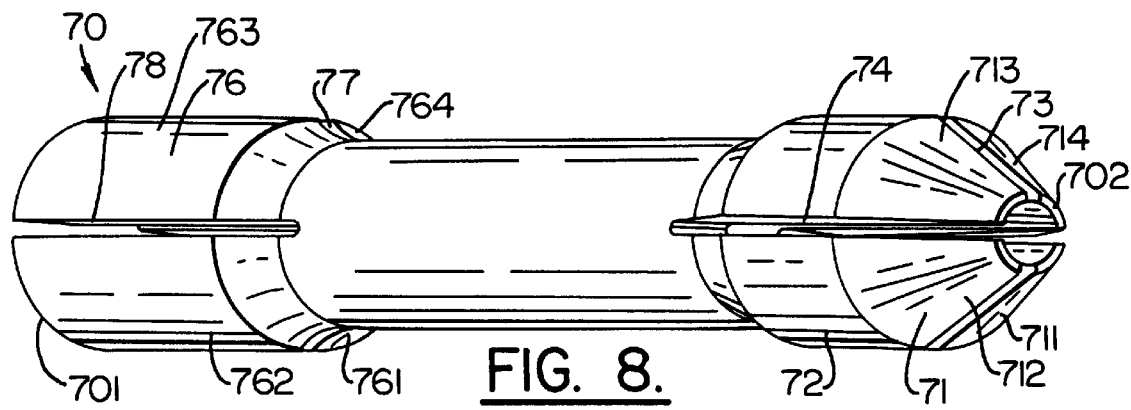
FIG. 8 is a perspective side view of a fourth embodiment, an all-collagen fastener with cut ends, in a dehydrated state.
Figure 9:
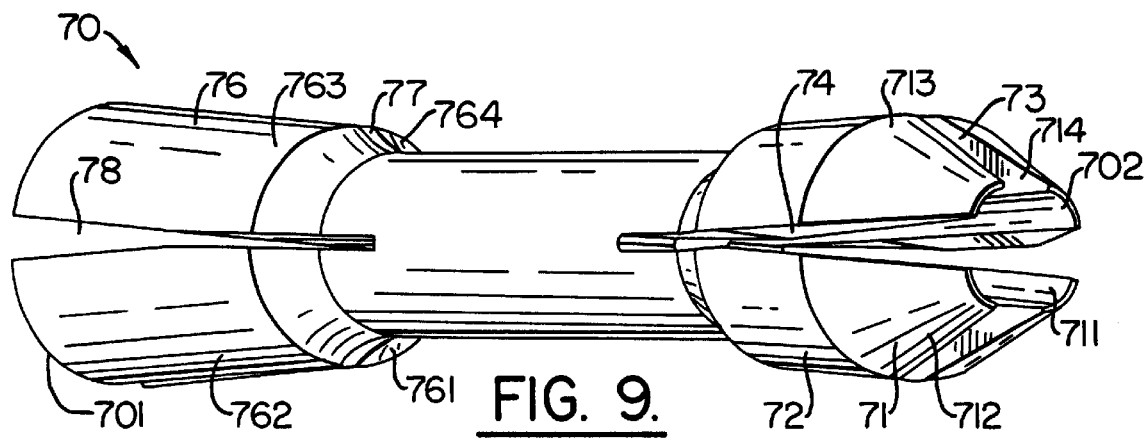
FIG. 9 is a perspective side view of the embodiment of FIG. 8 in a hydrated state.
Figure 10:
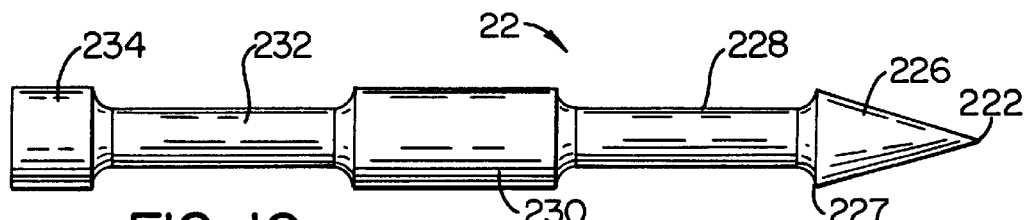
FIG. 10 is a perspective side view of the rigid polymer core of a fifth embodiment of a fastener.
Figure 11:
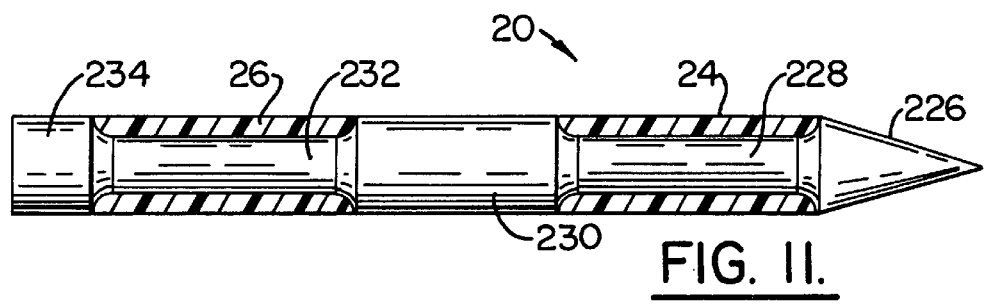
FIG. 11 is a perspective side view of the embodiment of FIG. 10 with two spaced-apart collagen bands.
Figure 12:
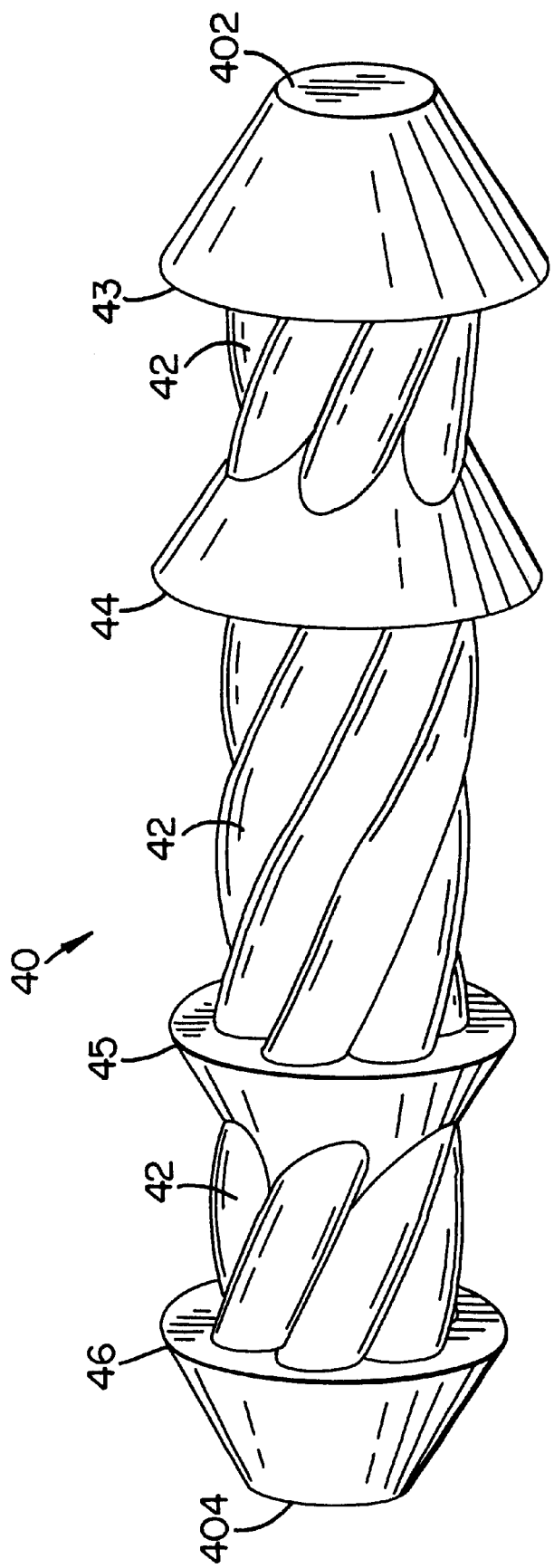
FIG. 12 is a perspective side view of a sixth embodiment, a fastener comprising resorbable suture material with two collagen rings at each end.

A fourth embodiment of the invention, which is illustrated in FIGS. 8 and 9, comprises an elongated generally cylindrical fastener 70, which comprises a biocompatible polymer. Fastener 70 has a first distal portion 71 that narrows toward a distal end 702, wherein the narrowed distal end 702 facilitates insertion into the soft tissue T. Similarly, the fastener 70 has a second distal portion 72 that extends in a proximal direction from the first distal portion 71.

A first distal slit 73 extends generally longitudinally from the distal end 702 into the second distal portion 72; a second distal slit 74 extends generally longitudinally from the distal end 702 into the second distal portion 72, the second distal slit 74 generally normal to the first distal slit 73. Thus the first 73 and the second 74 distal slits form four quarter-cylindrical distal sections 711–714.

Fastener 70 additionally has a proximal portion 76 that extends from the proximal end 701 in a distal direction.

A first proximal Lit 77 extends generally longitudinally from the proximal end 702 into the proximal portion 76; a second proximal slit 78 similarly extends generally longitudinally from the proximal end 701 into the proximal portion 76, the second proximal slit 78 generally normal to the first proximal slit 77. Thus the first 77 and the second 78 proximal slits form four quarter-cylindrical proximal sections 761–764.

The construction of the fastener 70 biases it to expand via the distal 73,74 and the proximal 77,78 slits between an insertion position (FIG. 8) wherein the distal sections 711–714 and the proximal sections 761–764 are closely opposed and a healing position (FIG. 9) wherein the distal sections 711–714 and the proximal sections 761–764 are flared. This flared position serves to bring two sides S1,S2 of a tear T into apposition, which promotes healing and further to forms an interference fit within the soft tissue MM to resist a removal of the fastener 70 therefrom.

A fifth embodiment of a fastener 20 comprises an elongated core 22 (FIG. 10) that has a distal conical portion 226 that has a narrowing cross section toward the distal end 222. As previously, this shape is for facilitating an insertion of the fastener 20 into soft tissue.

The core 22 also has a first narrowed generally cylindrical portion 228 that is adjacent and proximal of the distal portion 226. This portion 228 has a diameter less than the diameter of the proximal end 227 of the distal portion 226.

A widened generally cylindrical central portion 230 is situated adjacent and proximal of the first cylindrical narrowed portion 228. This portion 230 has a diameter larger than that of the first cylindrical portion 228.

A second narrowed generally cylindrical portion 232 is situated adjacent and proximal of the central portion 230. This portion 232 has a diameter less than that of the central portion 230.

Finally, a widened generally cylindrical proximal portion 234 is situated adjacent and proximal of the second cylindrical narrowed portion 232. This portion 234 has a diameter larger than that of the second cylindrical portion 232.

The first and the second narrowed portions 228,232 can thus be seen to form generally annular notches in the core 22.

Preferably the core 22 material comprises a plastic that is biocompatible with the soft tissue MM of the patient and further is biodegradable within a first time span greater than or equal to a second time span over which the sides S1,S2 of the tear T can knit together.

The fastener 20 additionally comprises (FIG. 11) a first collagen band 24 that is positioned in surrounding relation to the first cylindrical narrowed portion 228. Further, a second collagen band 26 is positioned in surrounding relation to the second cylindrical narrowed portion 232. As with previous embodiments of the fastener, the first and the second collagen bands 24,26 are expandable between a dehydrated state for insertion and a hydrated state for healing, and the first and the second collagen bands when hydrated bring two opposing sides S1,S2 of the tear T into apposition for promoting healing and further form an interference fit with the soft tissue MM, again retaining the fastener 20 in position. Preferably the first and the second collagen bands 24,26 each have a thickness adapted for forming a generally smooth outer surface, which also facilitates insertion. Also preferably, the collagen comprises a cross-linked bovine collagen.

A sixth embodiment 40 (FIG. 12) of a fastener comprises an elongated bioresorbable core 42 that preferably comprises a suture material.

Situated in surrounding relation to the core 42 are four generally conical bands, two 43,44 having a narrowing cross section toward the distal end 402 and two 45,46 having a narrowing cross section toward the proximal end 404. The distal band 43 is positioned in surrounding relation to a distal end (not shown) of the core 42; the proximal band 46 is positioned in surrounding relation to a proximal end (not shown) of the core 42.

A third band 44 is positioned in surrounding relation to the core 42 proximal of and in spaced relation to the distal band 43, and a fourth band 45 is positioned in surrounding relation to the core 42 distal of and in spaced relation to the proximal band 46. The third 44 and the fourth 45 bands are separated by a length of core 42 sufficient to breach the tear T.

The bands 43–46 each comprise a material expandable between a dehydrated state for insertion and a hydrated state for healing, for example, a collagen material such as bovine collagen.

The Fastener Insertion Method

Figure 13:
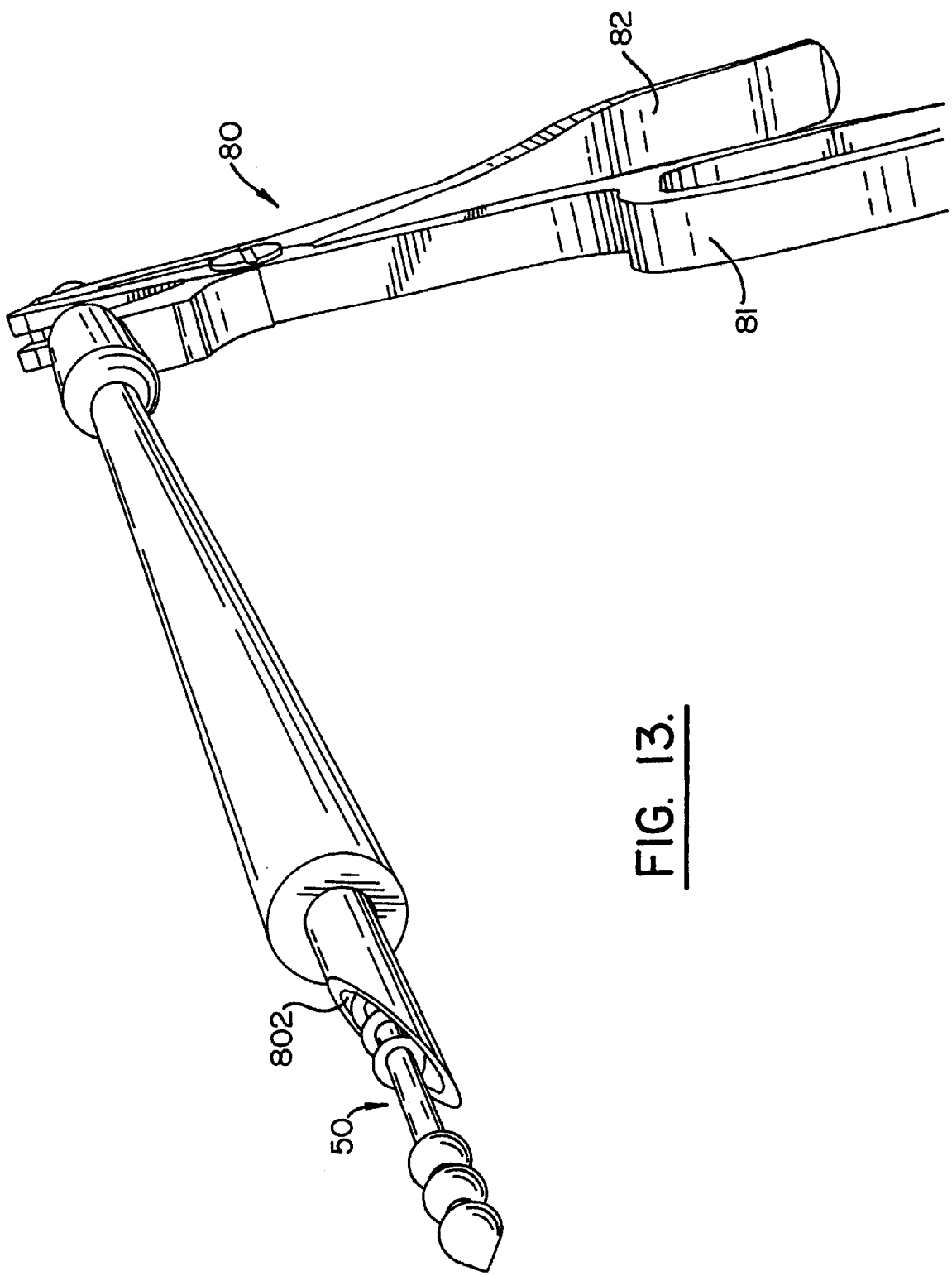
FIG. 13 illustrates a front-side perspective view of the third embodiment of the fastener being inserted into a delivery device.

The fastener insertion method of the present invention comprises a series of steps that are generally similar irrespective of which of the above-described fasteners containing collagen 10,20,30,40,50,70 is utilized. A device 80 for inserting a fastener, shown as fastener 50, is illustrated in FIG. 13. The fastener 50 is shown being placed inside the bore 802 of a cannula tube 80. A scissors-like action of the device handles 81,82 pushes the fastener 50 out of the bore for delivering the fastener 50 across a tear T.

Schematically the method is illustrated in FIGS. 14A–D: A cannula 92 having a pointed trocar 90 within its bore is driven across a tear T in a meniscus MM (FIG. 14A). The trocar 90 is removed from the surgical site (FIG. 14B). The fastener 30 is inserted down the cannula 92 (FIG. 14C) until it breaches the tear T. Then the cannula 92 is removed (FIG. 14D) leaving the fastener 30 across the tear T.

Next the method will be discussed and is illustrated (FIGS. 15–19) in greater detail with the second embodiment of the fastener 30 as an exemplary embodiment.

Figure 15:
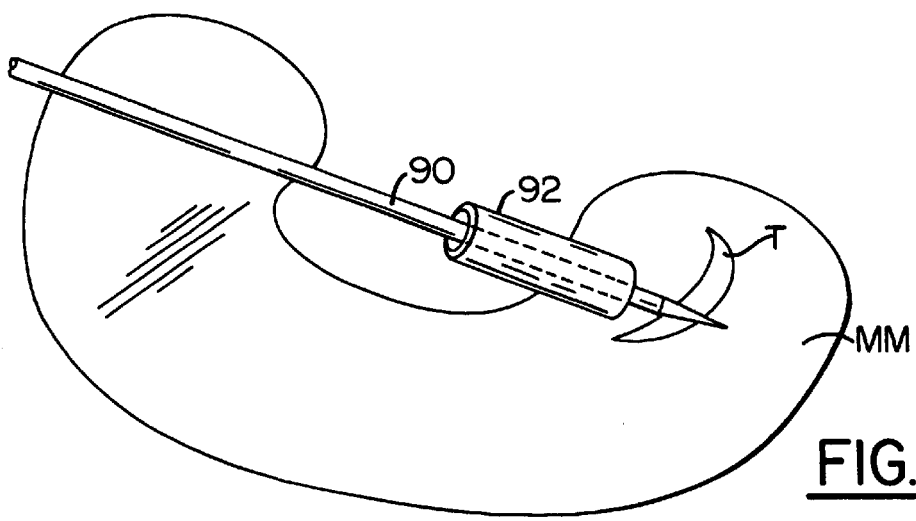
FIG. 15 illustrates a trocar being driven across the tear and a tube being passed over the trocar.

The first step of the method comprises driving a trocar 90, which typically comprises an elongated pointed instrument, across the tear T in a direction generally normal to the tear T (FIG. 15). Next a tube 92 is passed over the trocar 90 to a position wherein the tube 90 breaches the tear T. Then the trocar is removed from the soft tissue MM.

Figure 16:
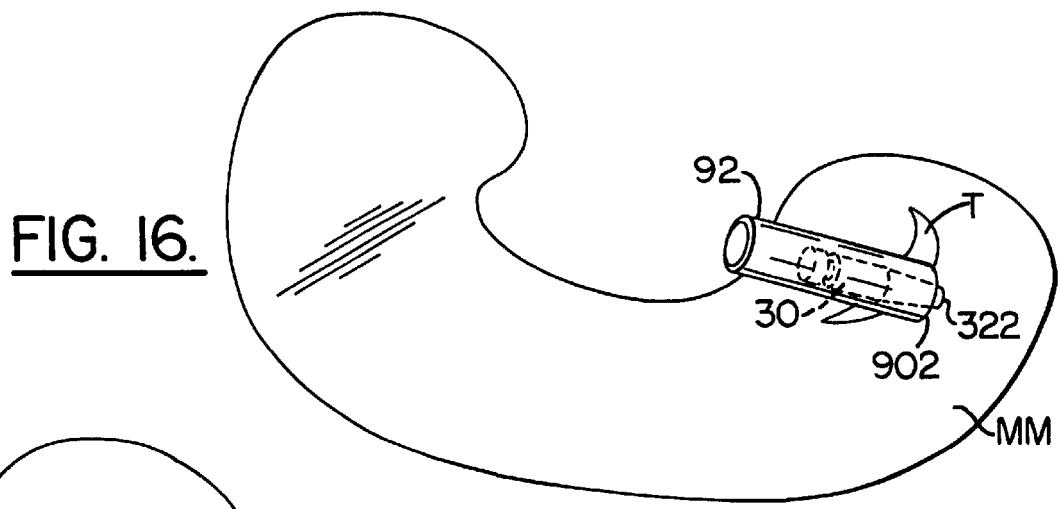
FIG. 16 illustrates the second embodiment of the fastener being pushed down the tube and across the tear.

A fastener 30 in a dehydrated state is introduced into the tube 92 and pushed to a position adjacent the tube's distal end 902 (FIG. 16). Next the tube 92 is removed from the soft tissue MM, leaving the fastener 30 in position to breach the tear T.

Figure 17:
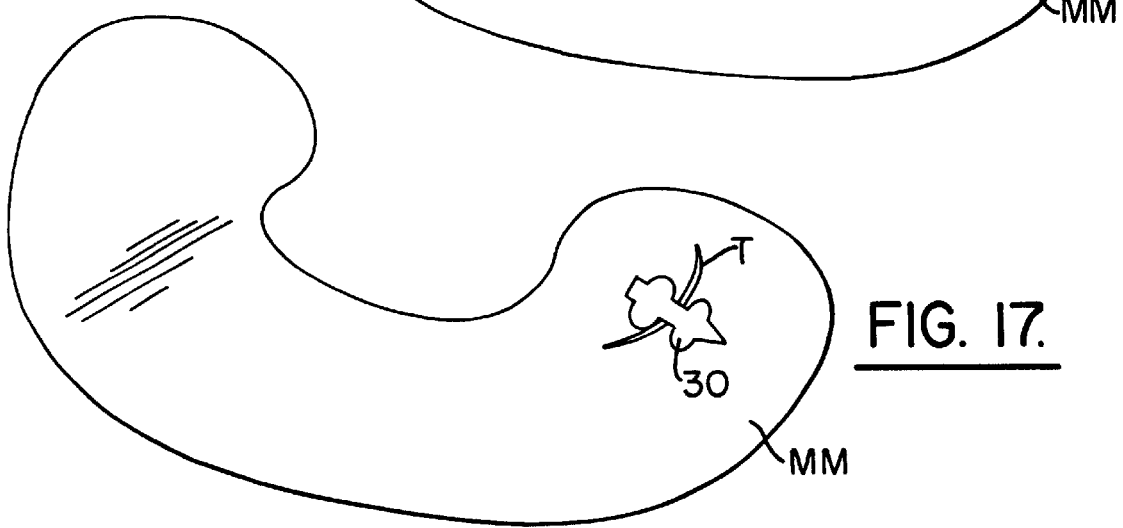
FIG. 17 illustrates the second embodiment of the fastener in place in a hydrated state, bringing the two sides of the tear into apposition.
Figure 18:
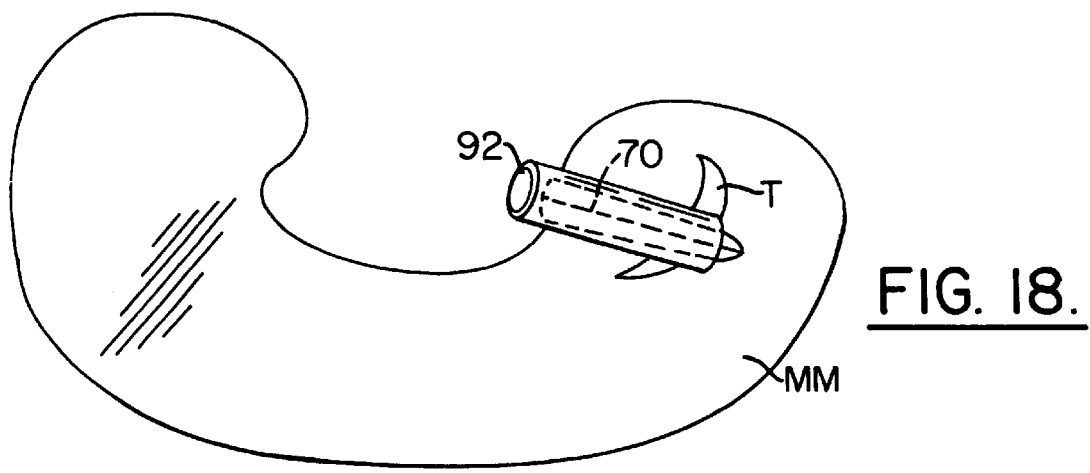
FIG. 18 illustrates the fourth embodiment of the fastener being pushed down the tube and across the tear.
Figure 19:
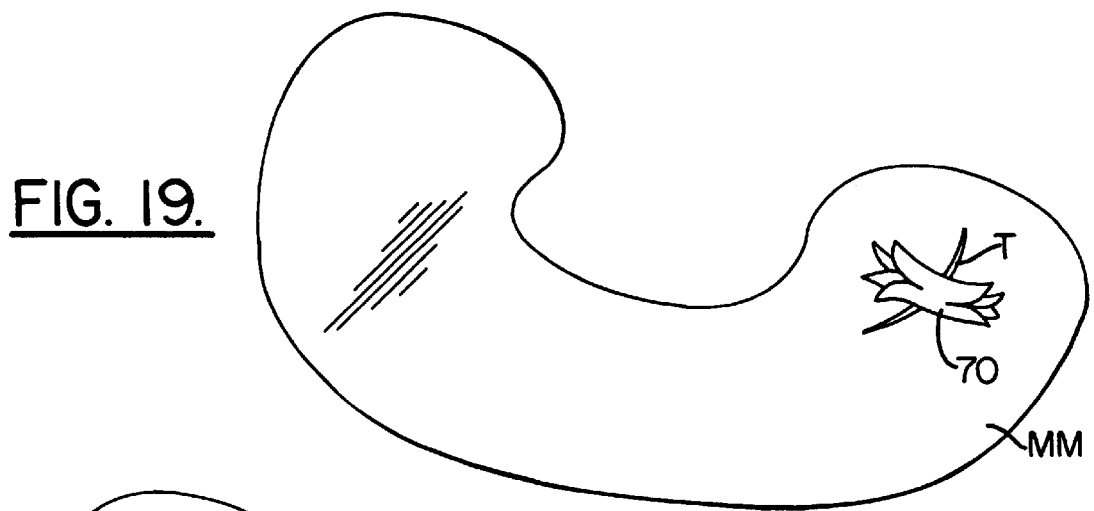
FIG. 19 illustrates the fourth embodiment of the fastener in place in the flared state, bringing the two sides of the tear into apposition.
Figure 20:
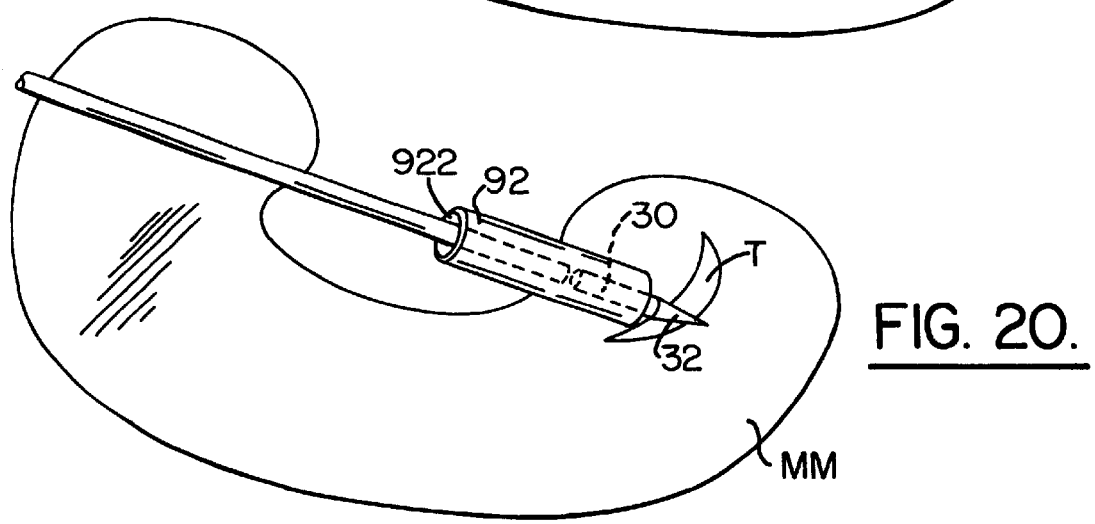
FIG. 20 illustrates an alternate embodiment of the method, with the soft tissue being pierced by the distal end of the fastener.

Finally, the fastener 30 is permitted to hydrate in situ, which causes the collagen bands 33,34 to swell, forming a structure similar to a dumbbell, which brings the opposing sides S1,S2 of the tear T into apposition and forming an interference fit between the fastener 30 and the soft tissue MM for retaining the fastener 30 in position (FIG. 17).

When the fastener 70, which comprises a nonexpandable polymer in a preferred embodiment, is utilized, the method comprises the same steps as above for preparing the site, including the trocar driving, tube positioning, and trocar removal steps (FIG. 14A–D).

For this embodiment, however, when the fastener 70 is passed down the tube 92 (FIG. 18), the tube 92 provides the means via close dimensioning for retaining the fastener 70 in the insertion position while the fastener 70 is being pushed down the tube 92. Then, when the tube 92 is removed, leaving the fastener 70 in position to breach the tear T, the distal sections 711–714 and proximal sections 761–764 flare to the healing position (FIG. 19) and to hold the two sides S1,S2 of the tear T into apposition as above.

In yet another embodiment of the method of the present invention, a trocar is not used; rather, fastener, for example, fastener 30, is inserted into the cannula bore 922 (FIG. 20), and is supported adjacent the cannula's distal end 902 with the fastener's pointed distal end 32 protruding therefrom. A rod 93 may be used to transmit force to the fastener 30, and the fastener's distal end 32 is used to pierce the tissue and breach the tear T. The following steps, as shown in FIGS. 16–19, remain substantially the same. A fastener to be used with this embodiment must have sufficient rigidity to pierce the tissue; consequently, fastener embodiments 10,20,30,50, 70 disclosed herein would be suitable for this method.

It may be appreciated by one skilled in the art that additional embodiments may be contemplated, including fasteners, systems, and methods for repairing other soft tissue tears, such as in the shoulder.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for repairing a tear in soft tissue comprising the steps of:

driving a trocar comprising an elongated pointed instrument across the tear in a direction generally normal to the tear;

passing a tube over the trocar to a position wherein the tube breaches the tear;

removing the trocar from the soft tissue;

introducing a fastener in a dehydrated state into the tube and pushing the fastener to a position adjacent a distal end of the tube, the fastener comprising:

an elongated core having:

a distal portion having a narrowing cross section toward a pointed distal end, for facilitating an insertion of the fastener into soft tissue; and a narrowed central portion extending between a proximal end and the distal portion; and a collagen band positioned in surrounding relation to the core central portion, the collagen band expandable between the dehydrated state and a hydrated state wherein the collagen band is shaped to bring two opposing sides of the tear into apposition;

removing the tube from the soft tissue, leaving the fastener in position to breach the tear; and permitting the fastener to hydrate in situ, causing the collagen band to swell, bringing the opposing sides of the tear into apposition and forming an interference fit between the fastener and the soft tissue for retaining the fastener in position.

2. A method for repairing a tear in soft tissue comprising the steps of:

driving a trocar comprising an elongated pointed instrument across the tear in a direction generally normal to the tear;

passing a tube over the trocar to a position wherein the tube breaches the tear;

removing the trocar from the soft tissue;

introducing a fastener in a dehydrated state into the tube and pushing the fastener to a position adjacent a distal end of the tube, the fastener comprising:

an elongated core having:

a first conical portion having a narrowing cross section toward a distal end, wherein in use an insertion of the fastener into soft tissue is facilitated by the narrowed distal end;

a second conical portion having a narrowing cross section toward a proximal end of the first conical portion; and a narrowed central portion extending between a proximal end and the second conical portion;

a first collagen band positioned in surrounding relation to the core central portion; and a second collagen band positioned in surrounding relation to at least a distal section of the second conical portion;

wherein the first and the second collagen bands are expandable between the dehydrated state and a hydrated state for healing, wherein the first and the second collagen bands when hydrated bring two opposing sides of the tear into apposition;

removing the tube from the soft tissue, leaving the fastener in position to breach the tear; and permitting the fastener to hydrate in situ, causing the collagen bands to swell, bringing the opposing sides of the tear into apposition and forming an interference fit between the fastener and the soft tissue for retaining the fastener in position.

3. A method for repairing a tear in soft tissue comprising the steps of:

driving a trocar comprising an elongated pointed instrument across the tear in a direction generally normal to the tear;

passing a tube over the trocar to a position wherein the tube breaches the tear;

removing the trocar from the soft tissue;

introducing a fastener in a dehydrated state into the tube and pushing the fastener to a position adjacent a distal end of the tube, the fastener having:

a first conical portion narrowing toward a distal end having a pointed tip;

a second conical portion proximal of and narrowing toward the first conical portion;

a narrowed central portion proximal of the second conical portion;

a third conical portion narrowing toward a proximal end;

a fourth conical portion distal of and narrowing toward the third conical portion;

wherein the fastener comprises a collagen material expandable between the dehydrated state and a hydrated state for healing;

removing the tube from the soft tissue, leaving the fastener in position to breach the tear; and permitting the fastener to hydrate in situ, causing the fastener to swell, the swollen conical portions bringing the opposing sides of the tear into apposition to promote healing and further forming an interference fit between the fastener and the soft tissue for retaining the fastener in position.

4. A method for repairing a tear in soft tissue comprising the steps of:

driving a trocar comprising an elongated pointed instrument across the tear in a direction generally normal to the tear;

passing a tube over the trocar to a position wherein the tube breaches the tear;

removing the trocar from the soft tissue;

introducing an elongated generally cylindrical fastener into the tube and pushing the fastener to a position adjacent a distal end of the tube, the fastener having:

a first distal portion narrowing toward a distal end for facilitating insertion into the soft tissue;

a second distal portion extending in a proximal direction from the first distal portion;

a distal slit extending generally longitudinally from the distal end into the second distal portion, forming two half-cylindrical distal sections;

a proximal portion extending from a proximal end in a distal direction;

a proximal slit extending generally longitudinally from the proximal end into the proximal portion, forming two half-cylindrical proximal sections;

wherein the fastener is biased to expand via the distal slit and the proximal slit between an insertion position wherein the distal sections and the proximal sections are closely opposed and a healing position wherein the distal sections and the proximal sections are flared; and removing the tube from the soft tissue, leaving the fastener in position to breach the tear and permitting the fastener distal sections and proximal sections to flare to the healing position, bringing the two sides of the tear into apposition for promoting healing and further forming an interference fit between the fastener and the soft tissue for retaining the fastener in position.

5. A method for repairing a tear in soft tissue comprising the steps of:

driving a trocar comprising an elongated pointed instrument across the tear in a direction generally normal to the tear;

passing a tube over the trocar to a position wherein the tube breaches the tear;

removing the trocar from the soft tissue;

introducing an elongated generally cylindrical fastener into the tube and pushing the fastener to a position adjacent a distal end of the tube, the fastener having:

a first distal portion narrowing toward a distal end for facilitating insertion into the soft tissue;

a second distal portion extending in a proximal direction from the first distal portion;

a first distal slit extending generally longitudinally from the distal end into the second distal portion;

a second distal slit extending generally longitudinally from the distal end into the second distal portion, the second distal slit generally normal to the first distal slit, the first and the second distal slits forming four quarter-cylindrical distal sections;

a proximal portion extending from a proximal end in a distal direction;

a first proximal slit extending generally longitudinally from the proximal end into the proximal portion;

a second proximal slit extending generally longitudinally from the proximal end into the proximal portion, the second proximal slit generally normal to the first proximal slit, the first and the second proximal slits forming four quarter-cylindrical proximal sections;

wherein the fastener is biased to expand via the distal slits and the proximal slits between an insertion position wherein the distal sections and the proximal sections are closely opposed and a healing position wherein the distal sections and the proximal sections are flared; and removing the tube from the soft tissue, leaving the fastener in position to breach the tear and permitting the fastener distal sections and proximal sections to flare to the healing position, bringing the two sides of the tear into apposition for promoting healing and further forming an interference fit between the fastener and the soft tissue for retaining the fastener in position.

6. A method for repairing a tear in soft tissue comprising the steps of:

introducing a fastener in a dehydrated state into a tube and pushing the fastener to a position adjacent a distal end of the tube, the fastener comprising:

an elongated core having:

a distal portion having a narrowing cross section toward a pointed distal end, for facilitating an insertion of the fastener into soft tissue; and a narrowed central portion extending between a proximal end and the distal portion; and a collagen band positioned in surrounding relation to the core central portion, the collagen band expandable between the dehydrated state and a hydrated state wherein the collagen band is shaped to bring two opposing sides of the tear into apposition;

driving the tube and fastener across the tear in a direction generally normal to the tear, the pointed distal end of the fastener piercing the soft tissue, to a position wherein the tube and the fastener breach the tear;

removing the tube from the soft tissue, leaving the fastener in position to breach the tear; and permitting the fastener to hydrate in situ, causing the collagen band to swell, bringing the opposing sides of the tear into apposition and forming an interference fit between the fastener and the soft tissue for retaining the fastener in position.

7. A method for repairing a tear in soft tissue comprising the steps of:

introducing a fastener in a dehydrated state into a tube and pushing the fastener to a position adjacent a distal end of the tube, the fastener comprising:

an elongated core having:

a first conical portion having a narrowing cross section toward a distal end, wherein in use an insertion of the fastener into soft tissue is facilitated by the narrowed distal end;

a second conical portion having a narrowing cross section toward a proximal end of the first conical portion; and a narrowed central portion extending between a proximal end and the second conical portion;

a first collagen band positioned in surrounding relation to the core central portion; and a second collagen band positioned in surrounding relation to at least a distal section of the second conical portion;

wherein the first and the second collagen bands are expandable between the dehydrated state and a hydrated state for healing, wherein the first and the second collagen bands when hydrated bring two opposing sides of the tear into apposition;

driving the tube and fastener across the tear in a direction generally normal to the tear, the pointed distal end of the fastener piercing the soft tissue, to a position wherein the tube and the fastener breach the tear;

removing the tube from the soft tissue, leaving the fastener in position to breach the tear; and permitting the fastener to hydrate in situ, causing the collagen bands to swell, bringing the opposing sides of the tear into apposition and forming an interference fit between the fastener and the soft tissue for retaining the fastener in position.

8. A method for repairing a tear in soft tissue comprising the steps of:

introducing a fastener in a dehydrated state into a tube and pushing the fastener to a position adjacent a distal end of the tube, the fastener having:

a first conical portion narrowing toward a distal end having a pointed tip;

a second conical portion proximal of and narrowing toward the first conical portion;

a narrowed central portion proximal of the second conical portion;

a third conical portion narrowing toward a proximal end;

a fourth conical portion distal of and narrowing toward the third conical portion;

wherein the fastener comprises a collagen material expandable between the dehydrated state and a hydrated state for healing;

driving the tube and fastener across the tear in a direction generally normal to the tear, the pointed distal end of the fastener piercing the soft tissue, to a position wherein the tube and the fastener breach the tear;

removing the tube from the soft tissue, leaving the fastener in position to breach the tear; and permitting the fastener to hydrate in situ, causing the fastener to swell, the swollen conical portions bringing the opposing sides of the tear into apposition to promote healing and further forming an interference fit between the fastener and the soft tissue for retaining the fastener in position.

9. A method for repairing a tear in soft tissue comprising the steps of:
  introducing a fastener in a dehydrated state into a tube and pushing the fastener to a position adjacent a distal end of the tube, the fastener having:
    a first distal portion narrowing toward a distal end for facilitating insertion into the soft tissue;
    a second distal portion extending in a proximal direction from the first distal portion;
    a distal slit extending generally longitudinally from the distal end into the second distal portion, forming two half-cylindrical distal sections;
    a proximal portion extending from a proximal end in a distal direction;
    a proximal slit extending generally longitudinally from the proximal end into the proximal portion, forming two half-cylindrical proximal sections;
    wherein the fastener is biased to expand via the distal slit and the proximal slit between an insertion position wherein the distal sections and the proximal sections are closely opposed and a healing position wherein the distal sections and the proximal sections are flared;
  driving the tube and fastener across the tear in a direction generally normal to the tear, the pointed distal end of the fastener piercing the soft tissue, to a position wherein the tube and the fastener breach the tear; and
  removing the tube from the soft tissue, leaving the fastener in position to breach the tear and permitting the fastener distal sections and proximal sections to flare to the healing position, bringing the two sides of the tear into apposition for promoting healing and further forming an interference fit between the fastener and the soft tissue for retaining the fastener in position.

10. A method for repairing a tear in soft tissue comprising the steps of:
  introducing a fastener in a dehydrated state into a tube and pushing the fastener to a position adjacent a distal end of the tube, the fastener having:
    a first distal portion narrowing toward a distal end for facilitating insertion into the soft tissue;
    a second distal portion extending in a proximal direction from the first distal portion;
    a first distal slit extending generally longitudinally from the distal end into the second distal portion;
    a second distal slit extending generally longitudinally from the distal end into the second distal portion, the second distal slit generally normal to the first distal slit, the first and the second distal slits forming four quarter-cylindrical distal sections;
    a proximal portion extending from a proximal end in a distal direction;
    a first proximal slit extending generally longitudinally from the proximal end into the proximal portion;
    a second proximal slit extending generally longitudinally from the proximal end into the proximal portion, the second proximal slit generally normal to the first proximal slit, the first and the second proximal slits forming four quarter-cylindrical proximal sections;
    wherein the fastener is biased to expand via the distal slits and the proximal slits between an insertion position wherein the distal sections and the proximal sections are closely opposed and a healing position wherein the distal sections and the proximal sections are flared;
  driving the tube and fastener across the tear in a direction generally normal to the tear, the pointed distal end of the fastener piercing the soft tissue, to a position wherein the tube and the fastener breach the tear; and
  removing the tube from the soft tissue, leaving the fastener in position to breach the tear and permitting the fastener distal sections and proximal sections to flare to the healing position, bringing the two sides of the tear into apposition for promoting healing and further forming an interference fit between the fastener and the soft tissue for retaining the fastener in position.

* * * * *